United States Patent [19]

Carr

[11] Patent Number: 5,509,968
[45] Date of Patent: Apr. 23, 1996

[54] DECONTAMINATION OF ORTHOPAEDIC IMPLANTS

[75] Inventor: James M. Carr, Cos Cob, Conn.

[73] Assignee: New York Society For The Ruptured And Crippled Maintaining The Hospital For Special Surgery, New York, N.Y.

[21] Appl. No.: 191,434

[22] Filed: Feb. 3, 1994

[51] Int. Cl.⁶ .............................. B08B 3/04; B08B 3/08; B08B 3/12
[52] U.S. Cl. .................. 134/1; 134/26; 134/28; 134/29; 134/3; 134/41; 134/40; 134/42; 134/19
[58] Field of Search .................. 134/26, 28, 29, 134/41, 42, 1, 3, 40, 19

[56] References Cited

U.S. PATENT DOCUMENTS

| | | | |
|---|---|---|---|
| 3,147,148 | 9/1964 | Goodin | 134/28 |
| 4,133,779 | 1/1979 | Hellyer et al. | 252/547 |
| 4,248,642 | 2/1981 | Kiyasu | 134/2 |
| 4,681,704 | 7/1987 | Bernardino et al. | 252/546 |
| 4,908,215 | 3/1990 | Perlman | 424/661 |
| 5,344,494 | 9/1994 | Davidson et al. | 134/42 |
| 5,350,458 | 9/1994 | Pinsl-Ober et al. | 134/22.1 |

*Primary Examiner*—Zeinab El-Arini
*Attorney, Agent, or Firm*—Darby & Darby

[57] ABSTRACT

Used or partially used orthopaedic implants or similar medical devices which have been in contact with animal tissue are decontaminated and made available for reuse by a three step process effective for removal of protein tissue, bone tissue, and lipids.

19 Claims, No Drawings

DECONTAMINATION OF ORTHOPAEDIC IMPLANTS

BACKGROUND OF THE INVENTION

It is common knowledge that great strides have been made in the area of orthopaedic medicine by the use of joint implants. The implants are usually metallic and often have porous surfaces. Not all implants, however, are successfully installed in the patient on the initial attempt, and it may be necessary to try two or more implants of different sizes or curvatures during the implant procedure before the desired fit is realized.

The unsuccessful implant in such cases has generally been discarded. Foreign proteins and lipids remain in the interstices of the porous surface of the implant. They can cause an adverse immune reaction in an implant recipient if the implant were reused in another patient. Up to now, these implants have not been reusable and have been simply discarded. Each implant costs more than $1,000, so the cost of such wasted implants at a hospital having an active orthopaedic practice can amount to many thousands of dollars per year—a significant loss in this era of medical cost containment.

None of the cleaning processes now in use have been successful in assuring the removal of all tissue, bone, proteins and lipids from the porous surfaces of the implant. Hospitals have heretofore used detergents for breaking apart lipid tissue components (but not necessarily for their removal from a porous metal surface), and an ultrasonic cleaning bath to enhance cleaning (see U.S. Pat. No. 3,291,640 as well as "Good Hospital Practice: Handling and Biological Decontamination of Medical Devices", issued by the Association for the Advancement of Medical Instrumentation, 1991). Normally, such cleaning treatments have been performed on smooth medical utensils and equipment, as opposed to porous surface implants or other medical devices inserted into the body and intended to be in contact with tissue). U.S. Pat. No. 4,248,642, which deals with the cleaning of laboratory equipment using sodium hypochlorite is also noted.

In the totally non-analogous art of removing resin paint deposited on carbon resistors, Goodin, U.S. Pat. No. 3,147,148, discloses a multi-step process wherein both sodium hypochlorite and nitric acid washes are used to remove paint and silver from a ceramic core.

Them thus exists a need for a simple and inexpensive process that will make it possible to reuse orthopedic implants and similar medical devices whose porous surfaces have become contaminated with protein tissue, bone tissue and lipids. Typical of such devices are titanium, stainless steel and cobalt chrome alloy implants. The present invention is directed to serving this need.

SUMMARY OF THE INVENTION

The present invention relates to a three step process for efficiently removing foreign proteins and tissue from the minute interstices of a porous normally metallic surface used in medical treatment, such as an orthopaedic implant, to completely decontaminate its surface and allow its reuse and further contact with the tissues of the body.

Each of the three steps employs the use of a standard ultrasonic cleaning system to enhance the effectiveness of each cleaning step.

1. Tissue Lipid Removal

The implant is suspended in an aqueous bath of detergent suitable for emulsifying lipids at elevated temperatures, such as 40°–60° C., and is typically treated for about 1 to 45 minutes by the use of an ultrasonic cleaning system. This step emulsifies tissue lipids removes them from the implant so that they do not inhibit the subsequent cleaning steps.

The solution in the treating container is discarded and the container and implant are washed with clean water. The implant is then treated as follows.

2. Bone Salt Removal

The same or another container is filled with a dilute acid capable of dissolving bone salts (e.g., calcium phosphate minerals that are deposited in the collagen matrix of the bone). Dilute nitric acid is preferred because it is relatively safe to use and is known to have no adverse side effects. Other agents able to perform the bone salt removal step in a safe manner may alternatively be employed. The implant is added to the container, and subjected to ultrasonic treatment for approximately the same period and temperature as Step 1, i.e., 40°– 60° C. for about 1 to 45 minutes. This procedure dissolves and removes bone salts which might otherwise interfere with the third step of the procedure, set forth below.

After treatment, the solution containing dissolved bone salts is discarded and the implant and container are again rinsed with clean water.

3. Remaining Tissue Removal

The implant is then subjected to a bath of an aqueous solution sodium hypochlorite of a concentration as sold for general cleaning purposes, e.g., a 5–10% concentration, i.e., household bleach. This step removes any remaining organic bone tissue as well as protein. An ultrasonic cleaning system is again used for about 1 to 45 minutes and is conducted at a temperature in the range of 40°–60° C. This step removes soft tissue and any remaining bone tissue. When this step is completed, the solution is discarded and both the implant and container rinsed with water.

To ensure complete decontamination, it is normally desirable to repeat the foregoing steps one or more times to ensure that all tissue and other contaminants are removed. After drying and visual inspection for cleanliness, the cleaning procedure is complete.

DETAILED DESCRIPTION OF THE INVENTION

While the present invention is particularly directed to the treatment of implants, normally of a metallic nature, which have been contaminated by contact with animal protein and bone tissue, it can be used for cleaning other types of medical devices or instruments having a roughened or porous surface and which have been in contact with, or contaminated by, protein and/or bone tissue, and/or lipids and are intended to be contacted with animal tissue.

A typical orthopedic implant (e.g. hip stem) is made out of a titanium or cobalt chrome alloy. Many of these implants are treated to render a non-smooth texture to their surfaces. These surface textures range from roughened to porous. A porous coating is provided by a layer of titanium, typically, although sometimes a chrome cobalt steel is used. The coating is generally 0.1 to 1 mm thick and extensively penetrated with open spaces, and bonded to the surface of orthopaedic implants. The purpose of this layer is to encourage the growth of tissue into the open spaces and thus mechanically secure the implant to the bone of the patient. Non-limiting examples of the orthopedic implants that can be cleansed using the present invention include knee joints and shoulder joints. The term "roughened porous surface medical devices" coming in contact with animal tissue is intended to cover all such medical products. It is these roughened porous surfaces that can entrap particles of protein or lipid materials.

Unless otherwise indicated, all percentages set forth in the specification are based on weight.

Ultrasonic Cleaner

In each of the three steps of the present invention, the implant is transferred to a metal or glass container, preferably metal, containing the treating solution. The container must permit ultrasonic energy to impinge on the metal device that is to be decontaminated. Thus, a suitable container for use in practicing the invention comprises a sealed container. The container with the implant (or similar element to be treated) held inside is suspended in a commercially available ultrasonic cleaning system tank which is well known to those skilled in the art. A preferred ultrasonic cleaning tank is model H-4HT-1014-6, sold by Crest Ultrasonics, Trenton, N.J. The ultrasonic tank contains water and a detergent (Crest 200). The model number of the Crest Ultrasonic generator is 4.G-500-6; its frequency is 40 khz and its power output is 500 watts average.

Step 1—Tissue Lipid Removal

The solution in which the contaminated implant is first treated is an aqueous bath of a detergent suitable for emulsifying lipids. Commercial dishwashing detergents having strong grease emulsifying properties and containing a combination of anionic and nonionic surfactants may be employed. Suitable commercially available examples include Liquid Joy, Dawn, and Wisk brands of detergents. Such detergents have strong lipid and grease emulsifying properties and contain anionic and nonionic surfactants.

The present detergent solution may also contain optional ingredients such as amphoteric surfactants, dispensing aids, detergent builders, sterilizing agents, etc.

All of the patent and literature disclosures identified in this specification are hereby incorporated by reference into the present specification.

Non-limiting examples of suitable detergents include the following:

(1) A detergent composition containing a water-soluble semi-polar organic nonionic detergent such as water-soluble amine oxides, phosphine oxides and sulfoxide in combination with an alkaline earth metal salt of an anionic detergent such as linear alkyl benzene sulfonates, $C_8$ to $C_{22}$ paraffin sulfonates, $C_8$ to $C_{22}$ olefin sulfonates, $C_8$ to $C_{22}$ alkyl glycerol ether sulfonates and $C_8$ to $C_{22}$ alkyl sulfates. Such compositions are described in U.S. Pat. No. 4,133,779 to James A. Hellyer et al.

(2) A liquid detergent composition containing 10 to 50% of an anionic detergent of water soluble salt (particularly the alkali, alkaline earth, ammonium and amine salt) of organic sulfuric reaction products having in their structure a $C_{10}$ to $C_{16}$ alkyl radical and a sulfuric acid ester radical. Such anionic detergent may be represented by the formula $RO(C_2H_4O)_xSO_3M$, where R is a $C_{10}$ to $C_{16}$ alkyl group, M is sodium, potassium, ammonium, monoethanol, diethanol or triethane ammonium, calcium and magnesium cations and mixtures thereof, and x defines the ethoxylate distribution. At least 50% of the unethoxylated surfactant should be in the magnesium salt.

The detergent composition will also normally contain 1 to 20% of a suds stabilizer. Such stabilizers are typically nonionic surfactants, such as ethylene oxide condensates, fatty acid amides and the amine oxide semi-polar nonionics. More specifically they may be: (a) the condensation product of a $C_{10}$ to $C_{18}$ aliphatic alcohol or a $C_6$ to $C_{15}$ alkyl phenol with ethylene oxide and $C_8$ to $C_{18}$ fatty acid amides. The foregoing anionic and nonionic surfactants are described in U.S. Pat. No. 4,316,824 to Eugene J. Pancheri.

(3) A detergent composition containing a semi-polar nonionic detergent, an alkaline earth metal salt of an anionic detergent and an amidoalkylbetaine. More specifically, it comprises:

(a) 1 to 6% nonionic detergent comprising water-soluble amine oxides having $C_8$ to $C_{18}$ alkyl or hydroxy alkyl moiety and two alkyl moieties selected from alkyl and hydroxyl alkyl groups of 1 to 3 carbon atoms;

(b) 10–50% of an alkaline earth metal salt of an anionic detergent selected from linear $C_9$ to $C_{15}$ alkyl benzene sulfonates, $C_8$ to $C_{22}$ alkyl or $C_8$ to $C_{22}$ alkyl ether sulfates; and (c) 0.5 to 6% of an acylamidoalkylbetaine.

The acylamidoalkylbetaine improves the ability of the nonionic/anionic detergents to emulsify grease. The foregoing compositions are described in U.S. Pat. No. 4,681,704 to Lowell W. Bernardino et al.

Typical ranges of detergent concentration, treating times and temperatures are shown in Table 1 below.

A preferred detergent for use in practicing the present invention is sold under the trademark "Liquid Joy" by the Procter & Gamble Company of Cincinnati, Ohio.

TABLE 1

|  | Broad Range | Preferred Range | Especially Preferred Range |
| --- | --- | --- | --- |
| Concentration of Detergent, water:detergent by volume | 150:1 to 250:1 | 180:1 to 220:1 | 190:1 to 210:1 |
| Treatment Temperature, °C. | 30 to 70 | 40 to 60 | 50 |
| Treating time (minutes) for each treatment period | 15 to 60 | 15 to 45 | 30 |

Step 2—Bone Salt Removal

Following ultrasonic treatment in the detergent bath, the implant is immersed into a moderate strength solution of an agent having the ability to dissolve bone salt. The agent, however, must be relatively safe to handle and not have adverse side effects on the implant or on humans if inadvertently not fully removed during the washing Step and Step 3. In the most typical case the agent will be nitric acid. Other acids such as hydrochloric, sulfuric, and acetic acids may also be used, but are less preferable than nitric acid.

The treating times, temperatures, and ultrasonic cleaning units employed, and the ranges of times and temperatures set forth in Table 1 are also applicable to Step 2. The concentration of the acid must be appropriately strong enough to remove bone salt within the treating period defined. Typically, an acid aqueous solution of between 5 and 20% by volume of acid, preferably between 7 and 13% by volume of acid is used, particularly when nitric acid is employed as the preferred cleaning agent. One preferred solution contains 7% by volume of nitric acid in water (i.e., full strength, 70% diluted 10:1).

Step 3—Final Tissue Removal

As described previously, after passing through Steps 1 and 2, and being suitably rinsed, the implant or similar device is immersed into an aqueous hypochlorite solution. While normally sodium hypochlorite is preferred, closely related alkali metal hypochlorites such as potassium or lithium hypochlorite, or alkaline earth metal hypochlorites may also be used. Conventional Clorox brand bleach (sodium hypochlorite aqueous solution) has been successfully employed. The treatment time for the step is as set forth in Table 1, however, treatment times of 15 to 45 minutes are preferred. This solution may be diluted, if desired.

As noted above, after the ultrasonic cleaning treatment baths in each of Steps 1 to 3, the implant or other device is removed from the respective treating solution which now contain all, or some portion of the protein and/or lipid and/or bone contaminants and the solution is discarded. The implant is rinsed with distilled water after each Step. Typically this rinsing is done with 40–60, especially 50, milliliters of distilled water per square centimeter of porous coated surface to be treated.

Normally it will be preferred, for the sake of safety to repeat the sequence of Steps 1 through 3 at least once to ensure complete removal of protein tissue, bone tissue and lipids before attempting to reuse the decontaminated medical device.

The following description of the decontamination process illustrates the effectiveness of the present invention in decontamination of orthopaedic implants:

EXAMPLES 1–5

Experimental coupons or samples were prepared by cutting five sections from the porous coated area of a commercial unused titanium acetabular cup used for mammalian implants. The coupons were subjected to repeated cleaning with steps 1–3 above (with weighing after each repetition until no weight change was observed when the final clean state was reached). This insured that the coupons would be completely clean and free of contaminants at the start of the procedure.

Three of the five coupons were smeared with muscle, blood and bone fragments using manual pressure and then weighed. This weight minus the weight of the clean coupon gave the weight of smeared tissue for each coupon. The two remaining coupons which were not contaminated with tissue were used as controls.

Each of the coupons was then subjected to the three step decontamination process with the time of treatment in each stage being varied within the range set forth in Table 1. For each step, the respective solution identified above was employed. Thus, the tissue and lipid removal stage step (Step 1) employed a 0.5% solution of Joy Liquid detergent; the bone salt removal step employed a 7% by volume solution of nitric acid; and the final tissue removal step employed an aqueous solution of sodium hypochlorite (Clorox bleach).

Step 1

Test coupons were immersed at a temperature of 50° C. in a 0.5% concentration of the commercial detergent Liquid Joy (which contains a combination of anionic and nonionic detergent as described previously in U.S. Pat. Nos. 4,133,779 and 4,316,824). After suspending the implant and solution in a container it was subjected to ultrasonic pressure waves for 30 minutes using the Crest ultrasonic cleaner heretofore described. The solution was discarded and the implants rinsed with distilled water.

Step 2

The treated test coupons were then immersed in a 7% by volume nitric acid solution and the ultrasonic cleaning process of Step 1 repeated at a temperature of 50° C. for an additional 30 minutes.

The treated coupons were then removed from the nitric acid solution, rinsed with distilled water and prepared for Step 3.

Step 3

The rinsed container was filled with undiluted Clorox (5.25% aqueous sodium hypochlorite solution). The test coupons were sealed within the container and suspended in the same ultrasonic tank described above to dissolve remaining tissue. After being subjected to ultrasonic treatment for 30 minutes at 50° C., the test coupons were separated from the solution and rinsed with distilled water.

After each cleaning Step, the coupons of Examples 1–5 were dried by exposure to hot air and weighed. This weight subtracted from their original starting weight (prior to being smeared with tissue, blood and bone) defined the weight of the residue remaining after decontamination. Residue amounts as little as 100 micrograms were detectable by this method. Based on these tests, the use of two complete cycles, wherein each of the three treatment steps of the process of the present invention was performed for 20 to 30 minutes, afforded good decontamination results. All contamination (detectable by weighing) was removed.

Thus, the overall preferred decontamination cycle was 2 to 3 hours, i.e., 20 to 30 minutes for each of steps 1–3 repeated twice. This time period will of course vary with the particular conditions used in each of the tissue lipid removal, bone salt removal and remaining tissue removal Steps. The relative time periods for each step may be varied as well as the number of overall cycles. In general, the steps of the invention may be repeated as many times as needed, until the desired decontamination level has been achieved. It will generally be necessary or desirable to remove all detectable (100 microgram level) quantities of bone, protein and lipid material from an implant, in the interest of hygiene and safety.

EXAMPLE 6

Radioactive Labelling

To determine the efficacy of the invention in cleaning protein, lipid and bone from metal implant surfaces, a radioactively labelled protein tracing method was developed as an alternative to the weight loss method described in Examples 1–5 above.

Solutions of proteins consisting of radioactively labelled amino acids were pipetted onto coupons similar to those used in Examples 1–5. Each coupon was immersed in a glass vial containing 20 milliliters of Clorox bleach (5.25% sodium hypochlorite) solution, which was being subjected to ultrasonic scrubbing at the time of immersion. For each coupon, one milliliter samples of Clorox were removed at different time intervals from the moment of immersion, and the concentration of radioactively labelled amino acids in each sample was measured with a scintillation counter. The concentrations of radioactively labelled amino acids in the bleach samples were used to calculate the amount of protein constituents in the entire volume of Clorox at each time interval. This amount, divided by the amount of protein constituents pipetted onto the coupons, as determined by calculation, was expressed as a percentage of protein constituents that had been removed from the coupon pores at the different time intervals. In five tests, an average of 94% of the protein was taken out of the coupons within four minutes.

This radioactive labelling technique has the advantage of allowing the continuous measurement of the protein removal process.

Tissue contamination can be measured by two additional assays: immunological and bioburden. These assays were performed to further illustrate that the decontamination method of the present invention reliably removes all harmful tissue contamination.

EXAMPLE 7

Immunological Assay of Decontaminated Implants

When foreign proteins activate immune system cells, one result is a proliferation of these cells. The capacity of decontaminated porous coupons to activate immune system cells was assayed by exposing these cells to coupons that had been contaminated with tissue and subsequently processed with the subject decontamination device, and then measuring any cell proliferation. A significant increase in cell proliferation was used as an indication of protein contamination.

Proliferating cells will incorporate $^3$H-thymidine, a radiolabel. This incorporation can be measured with a beta counter and used as an index of cell proliferation. This is a commonly used assay to measure cell proliferation.

Three porous coupons, of the type described in Examples 1–5, were contaminated with bovine bone, lipid, and soft tissue, and then processed with the subject decontamination method (as set forth above with respect to Examples 1–5). An additional two coupons were subjected to the decontamination process of the present invention as described above with respect to Examples 1–5, but were not contaminated with tissue. These coupons were used for controls, as described below.

Human peripheral blood mononuclear cell ("PBMC") cultures containing lymphocytes and monocytes were established in 12-well tissue culture plates. Each of the five coupons was placed in a separate well. Additionally, agents known to stimulate activation of immune system cells were placed in six of the wells. One well was used as a control (i.e., no coupon or stimulating agent added). The cultures were incubated for five days. A 200 microliter aliquot was removed from each well and incubated in a solution containing $H^3$-thymidine for sixteen hours. Cells that had proliferated in all the wells, from the time that the coupons and stimulating agents were added, would incorporate the $H^3$-thymidine. The incorporation of $H^3$-thymidine was measured with a beta counter. The results are based on two performances of this assay.

The PBMCs cultured with the stimulating agents were stimulated to incorporate significant amounts of $H^3$-thymidine, whereas the PBMCs cultured with the decontaminated porous coupons showed no significant difference in $H^3$-thymidine incorporation as compared to the control PBMCs. Moreover, the similarity of $H^3$-thymidine incorporation by PBMCs cultured with the two control coupons and the control well to which no coupons or stimulating agents were added, indicate that there is nothing in or on the coupons that is suppressing cell proliferation. These results suggest that, in terms of lymphocyte stimulatory capacity, the porous coupons are essentially immunologically inert.

EXAMPLE 8

Bioburden Evaluation of Decontaminated Implants

The gamma irradiation dosages used to sterilize implants, and the effectiveness of these dosages, are derived from the average bioburden of the implants. Bioburden is the number of viable microbes present on medical devices prior to radiation sterilization. Tissue contamination can increase the bioburden of an implant above the limit for which its sterilization dosage is effective, thus compromising sterility.

Bioburden evaluations were performed on five orthopaedic joint implants representing a wide range of masses, geometries, alloys and types of porous coating. These implants were as follows: a cobalt-chrome femoral hip stem coated with titanium beads, a cobalt-chrome femoral hip stem with titanium plasma spray, a titanium tibial tray with titanium beads, a titanium acetabular cup with titanium wire mesh, and a titanium acetabular cup with cancellous structured titanium pores. Four of these implants were contaminated with bovine bone, lipid and soft tissue. The fifth had been contaminated with human tissue in the operating room and subsequently autoclaved without removing the tissue; it received no further contamination. The implants were then processed with the subject decontamination method as described in Examples 1–5. No environmental controls or precautions were taken to avoid microbial contamination during handling. The implants were exposed to the air while awaiting, and during shipment the next day to the laboratory where the bioburden evaluation was performed. Thus, ample opportunity was provided for microbial contamination. This was a worst case test that exposed the implants to contamination in a way that would not be allowed in the routine processing of devices destined for implantation.

In addition, two porous implants were subjected to the decontamination method without being contaminated with tissue. A bacteriostatic evaluation was performed on these two implants to demonstrate that there were no bacteriostatic or fungistatic characteristics of the experimental implants that would inhibit the bioburden evaluation.

The mean total aerobic bioburden for the five implants was 258 colony forming units ("CFUs"). This average is well below the 1000 CFUs maximum allowed by the Association for the Advancement of Medical Instrumentation ("AAMI") guideline for validation of sterilization doses. The standards set by AAMI are generally accepted by the health industry and regulatory agencies.

After processing five tissue-contaminated implants with the subject decontamination method, even under substandard sanitary conditions, the bioburden of the implants conformed to the requirements of the AAMI guideline for validating the effectiveness of the 25 kiloGray gamma radiation sterilization dose typically used for implants.

As noted previously, while particularly suitable for treating roughened or porous metallic implants, the present invention may be used to decontaminate non-metallic implants or other medical devices such as synthetic organ transplants having a surface coming into contact with animal protein or tissue where reuse of the synthetic organ after contamination is desired. While normally used for decontamination of medical devices used in humans, the method of the present invention can also be employed used in veterinary practice where similar problems are encountered by virtue of exposure to protein and/or bone tissue and where it is also desired to decontaminate and reuse an implanted device.

What is claimed is:

1. A process for decontaminating the surface of a medical implant which has been exposed to animal protein and/or bone tissue, and thereby exposed to lipids and bone salts, which comprises the sequential steps of:

(1) Immersing the surface in a bath containing a detergent suitable for emulsifying lipids at an elevated temperature, to remove lipids from the contaminated implant surface;

(2) immersing the surface in a bath containing an acidic agent capable of removing bone salts, to remove bone salts from the contaminated medical implant surface; and (3) Immersing the surface in a hypochlorite bath.

2. The process of claim 1 which comprises exposing said implant to ultrasonic energy during each of said steps.

3. The process of claim 2 wherein the surface of the implant is porous or roughened.

4. The process of claim 1 wherein step (2) employs a dilute nitric acid bath.

5. The process of claim 4 wherein a concentration of dilute nitric acid is 5 to 20 volume percent.

6. The process of claim 1 wherein step (3) employs a 3 to 15 weight percent aqueous solution of sodium hypochlorite.

7. The process of claim 1 wherein step (1) employs a 180:1 to 220:1 by volume aqueous solution of a detergent composition having strong grease emulsifying properties and containing a combination of nonionic and anionic detergents.

8. The process of claim 1 wherein each of steps (1) to (3) are performed at a temperature in the range of 40° to 60° C. for a period of between 15 and 45 minutes.

9. The process of claim 1 wherein said medical implant is a metallic orthopaedic implant having a porous surface.

10. The process of claim 1 which comprises repeating said steps at least twice to ensure complete decontamination.

11. A process for treating a roughened surface orthopaedic implant intended to be inserted into the human body and which has been contaminated with human protein and/or bone tissue, and thereby contaminated with lipids and bone salts, to make said implant reusable which comprises subjecting the implant to the following sequential steps:

(1) exposing the implant to a bath comprising a detergent suitable for emulsifying lipids at an elevated temperature, to remove lipids from the contaminated medical implant surface;

(2) contacting said implant with a dilute aqueous solution of nitric acid at an elevated temperature, to remove bone salts from the contaminated medical implant surface;

(3) contacting said implant with an aqueous solution of sodium hypochlorite at an elevated temperature and conducting steps (1)–(3) while said implant is exposed to ultrasonic treatment in an ultrasonic cleaning unit; whereby said implant is sufficiently decontaminated to be reused as an implant for introduction into a human body.

12. The process of claim 11 which comprises repeating each of said steps for between 15 and 45 minutes at a temperature between about 40° and about 60° C.

13. The process of claim 11 wherein said process is repeated so that the implant is sequentially treated by each step at least twice.

14. The process of claim 11 wherein step 2 employs a 5 to 20 volume percent aqueous solution of nitric acid.

15. The process of claim 11 wherein step 3 employs a 3 to 15 weight percent aqueous solution of sodium hypochlorite.

16. The process of claim 11 wherein step (1) employs a 180:1 to 220:1 by volume aqueous solution of a detergent composition having strong grease emulsifying properties and containing a combination of nonionic and anionic detergents.

17. The process of claim 11 wherein the orthopaedic implant is made of titanium.

18. The process of claim 11 wherein the orthopaedic implant is made of cobalt chrome alloy.

19. The process of claim 11 wherein each of said steps is sequentially repeated at least twice with each step being conducted at a temperature of between 40° and 60° C. for a period of time between about 15 and about 45 minutes.

\* \* \* \* \*